United States Patent [19]

Menachemoff et al.

[11] 4,305,932

[45] Dec. 15, 1981

[54] 1-ACYLETHOXYQUIN COMPOUNDS AND COMPOSITIONS FOR TREATING VITAMIN E-DEFICIENCY

[75] Inventors: Emil Menachemoff, Tel-Aviv; Oded Awerbuch; Raphael R. G. Haber, both of Givatayim, all of Israel

[73] Assignee: Abic Ltd., Israel

[21] Appl. No.: 871,455

[22] Filed: Jan. 23, 1978

[30] Foreign Application Priority Data

Jan. 27, 1977 [IL] Israel ................................. 51342

[51] Int. Cl.³ .................... A61K 31/47; C07D 215/26
[52] U.S. Cl. .................................. 424/180; 424/258; 536/23; 546/177; 546/178
[58] Field of Search .......... 536/23; 260/287 T, 287 L, 260/287 F, 286 Q, 45.8 N, 45.8 W; 424/258, 180; 546/177, 178

[56] References Cited

U.S. PATENT DOCUMENTS

| | | | |
|---|---|---|---|
| 2,426,012 | 11/1945 | Friedman et al. | 536/23 |
| 2,637,727 | 5/1953 | Hodge | 536/23 |
| 3,276,957 | 10/1966 | Rybak | 424/180 |
| 3,705,147 | 12/1972 | Robins et al. | 536/23 |
| 4,006,178 | 2/1977 | Stagi et al. | 260/287 T |

FOREIGN PATENT DOCUMENTS

| | | | |
|---|---|---|---|
| 745461 | 2/1970 | Belgium . | |
| 2802630 | 8/1978 | Fed. Rep. of Germany | 546/178 |
| 1260234 | 1/1972 | United Kingdom . | |

OTHER PUBLICATIONS

Magnin et al., *Tetrahedron, vol. 26, pp. 4019–4029 (1970)*.

*Primary Examiner*—Donald G. Daus
*Assistant Examiner*—D. B. Springer
*Attorney, Agent, or Firm*—Steinberg & Raskin

[57] ABSTRACT

The present invention deals with derivatives of 6-ethoxy-1,2,-dihydro-2,2,4-trimethylquinoline (called "Ethoxyquin"), processes for their preparation and their utility inter alia, as active ingredient of a pharmaceutical composition. Said compounds have, inter alia, under biological conditions anti-oxidant properties, may be used to protect Vitamin-E-deficient animals, and act as growth promoting agents.

32 Claims, No Drawings

1-ACYLETHOXYQUIN COMPOUNDS AND COMPOSITIONS FOR TREATING VITAMIN E-DEFICIENCY

The present invention relates to 6-ethoxy-1,2-dihydro-2,2,4-trimethylquinoline (hereinafter called "Ethoxyquin") derivatives.

It is known that Ethoxyquin is an antioxidant and inter alia, acts like Vitamin E in many biological functions. It is also known that it protects Vitamin E-deficient mice and piglets against iron toxicity (see e.g. Nature, 846 (1964); Acta Agriculture Scandinavica Suppl. 19 (1973) and in some cases is more efficient than Vitamin E itself.

Ethoxyquin also acts as a growth promoting agent when added to poultry feed (see Quarterly Jrnl. Fla. Acad. Sci. 27 (2), 131 (1964)).

However, Ethoxyquin has certain drawbacks. It is very difficult to produce and store Ethoxyquin in its purest form. It is an oil which rapidly and continuously darkens on storage. Moreover, it has an unpleasant taste. It is a base and the administration thereof causes problems.

It has therefore been desirable to find compounds for biological uses, which would have under biological conditions the above advantages of Ethoxyquin but not its disadvantages. It should, under biological conditions, have anti-oxidant properties, be able to protect Vitamin-E-deficient animals, e.g., from iron poisoning, act as growth promoting agent, inhibit amyloidesis, have no undesirable odour or taste, and in particular, there should be a possibility to obtain it in a pure and suitable form, for pharmaceutical compounding, i.e., as crystals, in powder form, or as a pure oil and syrup.

The present invention thus consists in ethoxyquin derivatives of general formula I

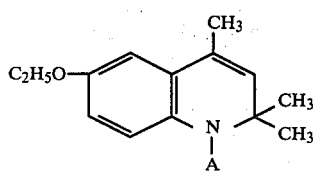

in which A stands for one of the following groups

I.

B standing for a. $(CHOR')_nR$ in which $R'$ stands for H, acyl, alkyl or aralkyl radical; R stands for $CH_2OH$, carboxyl, carboxylalkyl, carboxyaryl, carboxyaryl-alkyl, carboxamide radical; for $COR'''$, $R'''$ standing for the ethoxyquin radical; or for $CH_2OR''$, $R''$ standing for an acyl, aralkyl or alkyl radical; and n stands for an integer of 2-6.

b. $(CHR'''')_mN^+R_1R_2R_3X^-$ in which $R''''$ stands for H, a substituted or unsubstituted alkyl, aryl, aralkyl heterocyclic radical and for $(CH_2)_qCOOH$, where $q=1-3$; $R_1$, $R_2$ and $R_3$ stand for the same or different H, a substituted or unsubstituted alkyl, cycloalkyl, aryl or heteroaryl radical and any two radicals of $R_1$, $R_2$ and $R_3$ together with the N atom may form a heterocyclic radical; X stands for a non-toxic and physiologically acceptable salt forming anion; and m standing for an integer from 1-6;

c. $(CHR'''')_mNR_1R_2$ in which $R''''$, $R_1$, $R_2$ and m have the same meaning as above and $R_2$ can also stand for a suitable N-blocking group;

d. $NR'_1R'_2$ in which $R'_1$ and $R'_2$ stand for the same or different substituted or unsubstituted alkyl, cycloalkyl, aryl or heteroaryl radical, for 2 hydrogen atoms or together with the N atom may form a heterocyclic radical;

e. $OR_4$ in which $R_4$ stands for aryl, alkyl, polyhydroxycycloalkyl alkyl, or for

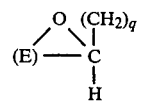

in which E stands for

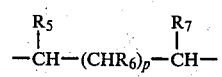

$R_5$, $R_6$ and $R_7$ standing for the same or different H, $CH_2OH$, $CH_2OAcyl$, OH, OAcyl, NHAcyl, $NH_2$, $N^+H_3X^-$, X having the same meaning as above, or one of them for $COOR_8$, in which $R_8$ stands for hydrogen, substituted or unsubstituted alkyl, cycloalkyl, aryl or aralkyl; p stands for an integer of 1 or 2, and q stands for an integer of 0 or 1;

f.

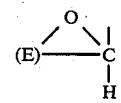

in which E has the same meaning as above; and g. halogen; or

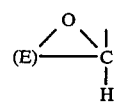

II.

in which E has the same meaning as above, excluding the possibility that a. $R_8$ stands for H; and
b. $R_5$, $R_6$ and $R_7$ stand for $N^+H_3X^-$, in which E has the same meaning as above; or the preparation of compounds of general formula I.

Thus, the process for the preparation of compounds of general formula I, in which A stands for

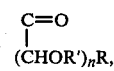

and in which n, $R'$ and R have the same meaning as in general formula I, are prepared by a process which consists in the reaction of ethoxyquin with an acid halide bearing protected hydroxyl groups in the presence of an acid acceptor and from the compound obtained the protecting groups and, if desired, are split off by methods known per se.

The reaction is performed preferably in an inert solvent, e.g. benzene or ether.

It may be performed at room temperature but is preferably performed at an elevated temperature, i.e., at the boiling point of the solvent, if any.

As acid acceptor there may be utilized for example, triethylamine, N,N-dimethylaniline, potassium carbonate, and even ethoxyquin itself in excess.

As hydroxyl-protecting groups there may be utilized, for example, alkyl, aralkyl, or acyl groups, like methyl, benzyl, acetyl or benzoyl groups.

The acylated products are soluble in organic solvents such as methanol, ethanol, acetone, dioxane, benzene, toluene and also propylene glycol, polyethylene glycol.

Compounds of general formula I in which A stands for either

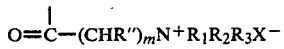

or $O\!=\!C\!-\!(CHR'''')NR_1R_2$ in which $R''''$, $R_1$, $R_2$, $R_3$, $X$ and m have the same meaning as in general formula I may be prepared by a process which consists in the reaction of ethoxyquin with an acyl halide bearing a protected amino group and actually splitting the protecting group off by methods known per se and, if desired, converting the salt, if obtained, into the free base.

As protecting group there may be utilized, for example, a benzyloxycarbonyl or t-butoxycarbonyl group. Said group may be split off by methods known per se, e.g. in the presence of suitable catalyst.

Compounds of general formula I in which A stands for $O\!=\!C\!-\!NR'_1R'_2$, in which $R'_1$ and $R'_2$ have the same meaning as in general formula I may be prepared by a process which consists in the reaction of 1-chlorocarbonyl-6-ethoxy-1,2-dihydro-2,2,4-trimethylquinoline with ammonia or a suitable amine, in or without the presence of a suitable anhydrous solvent, e.g. benzene, acetone, at ambient or elevated temperatures, preferably at 40°–140° C.

Compounds of general formula I in which A stands for

in which E has the same meaning as in general formula I may be prepared by a process which consists in the reaction of ethoxyquin with a glycosyl halide bearing protected hydroxyl groups and protected amino groups, if any, in the presence of an acid acceptor.

The process may be performed in an inert organic solvent, e.g. acetone, methyl-ethyl ketone or dioxane or without any solvent.

It may be performed at ambient or elevated temperature.

As acid acceptor there may be utilized an organic base, e.g. triethylamine, N,N dimethylaniline or even ethoxyquin in excess or an inorganic base, such as potassium carbonate.

As hydroxyl or amino-protecting group there may be utilized any of the groups indicated above. Said group may be split off by methods known per se.

Compounds of general formula I in which A stands for

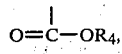

in which $R_4$ has the same meaning as in general formula I may be prepared by a process which consists in the reaction of 1-chlorocarbonyl-6-ethoxy-1,2-dihydro-2,2,4-trimethylquinoline with a compound of general formula $R_4OH$ in which $R_4$ has the same meaning as in general formula I in the presence of an acid acceptor and, if desired, splitting off the protecting groups of polyhydroxyl compounds, if any.

The reaction is advantageously performed at elevated temperature, preferably at 60°–140°.

The reaction may be performed without a solvent. However, it may be performed also in an inert solvent, such as hydrocarbons, e.g. toluene; ethers, e.g. dioxane; ketones, e.g. methyl-ethyl-ketone.

As acid acceptors there may be used those utilized in the previous reactions.

The compounds of general formula I in which A stands for $O\!=\!C\!-\!Hal$, Hal standing for a halogen atom serve as starting materials and/or intermediates for the preparation of some of the other compounds of general formula I. They are prepared, for example, in case that Hal stands for a halogen atom, by a reaction ethoxyquin with phosgene.

It has been found that compounds of general formula I can be obtained in crystalline or amorphous form, can be easily purified and obtained in a high degree of purity. These compounds are colourless and tasteless. They are stable and do not darken during storage. They are soluble to different extents in many organic solvents -e.g. chloroform, dioxane, methanol, ethanol, isopropanol, benzene, ether, propyleneglycol, polyethylene glycol, dimethylformamide, N,N-dimethyl-acetamide, isopropylideneglycerol and glycerolformal. Some of them are also soluble to a certain extent in water.

Some of the compounds of general formula I undergo slow hydrolysis when dissolved in water forming an extremely fine and stable emulsion in which the ethoxyquin droplets formed are of micron size.

It has been proved as will be shown later on, that when certain compounds of general formula I are administered to Vitamin E-deficient mice, they can protect them from iron poisoning caused by a concurrent administration of an iron preparation. In other words, the Vitamin E-deficient mice are protected against iron poisoning and the biological efficacy of the compounds is thus demonstrated.

The compounds of general formula I may be administered either separately or simultaneously with an iron preparation, e.g. iron dextran, or in the form of a mixture therewith. This is very important as in modern husbandry said iron preparation is administered to new born animals to prevent anaemiaand the animals may suffer from Vitamin E-deficiency.

The compounds of general formula I may be administered in many ways. Thus, they may be admixed to the feed. Another form of administration of those compounds of general formula I which are water soluble or suspendable is as part of drinking water. In some cases said compounds may be administered also in the form of an injection.

The present invention thus consists also in pharmaceutical preparation (human and veterinary) containing as active compound a compound of general formula I and in addition those in which B stands for $NR_1'R_2$ one of $R_1'$ or $R_2$ standing for hydrogen and the other having the same meaning given above.

The present invention thus consists also in a feed additive or additive to the drinking water of animals containing a compound of general formula I and in addition those in which B stands for $NR'R''$ one of $R'$ or $R''$ standing for hydrogen and the other having the same meaning given above.

The present invention will now be illustrated by the following Examples without being limited by them. In these examples all temperatures are given in degrees centigrade. All melting points are uncorrected.

EXAMPLE 1

Ethoxyquin (240 g) and 2,3,4,6-tetra-O-acetyl-α-D-glucopyranosyl bromide (228 g) were stirred at 80° for 18 hours. Acetone (200 ml) was added to the hot reaction mixture and stirring continued for an additional 20 minutes. After cooling, the solid ethoxyquin hydrobromide was filtered off, washed thoroughly with acetone and the combined acetone filtrates were evaporated under reduced pressure. The resulted crude product was recrystallised (iso-propanol) to yield 226.5 g of 1-(2,3,4,6-tetra-O-acetyl-D-glucopyranosyl)-6-ethoxy-1,2-dihydro-2,2,4-trimethylquinoline. m.p.: 180°–181°.

$v_{max}^{KBr}$: 3.30; 5.65; 6.15; 6.30; 6.65; 6.70; 6.90; 7.00; 7.20; 7.30; 7.40; 7.65; 7.75; 8.00; 8.35; 8.50; 8.60; 9.10. 9.00; 9.35; 9.60; 10.10; 10.40; 10.45; 10.90; 11.25; 11.65; 11.95; 12.15; 12.90; 13.30; 13.70; 14.85µ.

$\delta CDCl_3$: 1.10 s(3H); 1.38 t(J=7.0 Hz; 3H); 1.43 s(3H); 1.78 s(3H); 1.85 s(6H); 2.03 s(3H); 2.08 s(3H); 3.55–4.33 m, 4.70–5.55 m(10H); 6.55–6.80 m(2H); 7.15–7.40 m(1H) ppm.

The compound was colourless, odourless and tasteless.

EXAMPLE 2

1-(2,3,4,6-tetra-O-acetyl-D-glucopyranosyl)-6-ethoxy-1,2-dihydro-2,2,4-trimethylquinoline (35 g) was suspended in absolute $CH_3OH$ (350 ml). $NaOCH_3$(2,2 M, 2 ml) was added to the stirred reaction mixture. Dissolution of the solid was completed after 110 minutes. The solution was neutralized by acidic resin (Amberlite IR-120 (H+), then filtered, and the filtrate was evaporated under reduced pressure, leaving a white, amorphous solid being 24.2 g of 1-D-glucopyranosyl-6-ethoxy-1,2-dihydro-2,2,4-trimethylquinoline (hereinafter called "ethoxyquin-glucoside"). The compound was odourless.

$v_{max}^{KBr}$: 2.45; 3.40; 6.20; 6.35; 6.70; 7.20; 7.70; 7.90; 8.25; 8.50; 9.25; 9.50; 9.90; 10.30; 10.70; 11.15; 11.45; 12.30; 13.00; 13.40; 13.70µ.

$\delta CDCl_3$: 1.00–1.50 m (9H); 1.93 m (3H); 2.80–5.10 m (13H); 5.45 m (1H); 6.45–6.80 m (2H); 7.0–7.35 m (1H) ppm.

EXAMPLE 3

2,3,4,5,6-penta-6-acetyl-D-gluconyl chloride (12.0 g) was added to a solution of Ethoxyquin (12.4 g) in benzene (65 ml). The reaction mixture was stirred for 72 hours at room temperature followed by reflux (4 hours). The precipitate (6-ethoxy-1,2-dihydro-2,2,4-trimethylquinolinium hydrochloride) was filtered off, and the filtrate was evaporated to a constant weight under reduced pressure. The oily product was purified by chromatography on a silica column (ethylacetate-benzene 1:9), yielding 14.1 g of a light yellow, viscous syrup being 1-(2,3,4,5,6-penta-O-acetyl-D-gluconyl)-6-ethoxy-1,2-dihydro-2,2,4-trimethylquinoline (hereinafter called "ethoxyquin-gluconamide pentacetate").

$v_{max}^{NaCl}$: 3.45; 5.80; 6.00; 6.25; 6.40; 6.75; 7.05; 7.40; 7.60; 8.30; 8.65; 9.05; 9.60; 10.50; 11.50–12.40; 13.30µ.

$\delta CDCl_3$: 1.20 s(3H); 1.45 t(J=7Hz; 3H); 1.68 s(3H); 1.98–2.08 m(15H); 2.20 s(3H); 3.53–4.26 m(4H); 4.84 m(1H); 5.21 m(2H); 5.57 m(1H); 6.05 m(1H); 6.70–6.84 m(2H); 7.33–7.48 m (1H) ppm.

EXAMPLE 4

To a solution of 1-(2,3,4,5,6-penta-O-acetyl-D-gluconyl)-6-ethoxy-1,2-dihydro-2,2,4-trimethylquinoline (14.1 g) in abs. $CH_3OH$ (150 ml), 2.56 M $NaOCH_3$(1.56 ml) was added. The solution was stirred at room temperature (15 minutes) then neutralized with glacial acetic acid. The solution was filtered and evaporated to dryness under reduced pressure. The resulted crude product was purified on a Silica column ($CH_3OH$-$CHCl_3$ 3:7). 8.3 g of a highly viscous light yellow syrup being 1-D-gluconyl-6-ethoxy-1,2-dihydro-2,2,4-trimethylquinoline (hereinafter called "ethoxyquin gluconamide") was obtained. On standing or trituration an amorphous powder was obtained, with no odour.

$v_{max}^{KBr}$: 3.10; 3.45; 6.15; 6.40; 6.85; 7.10; 8.10; 8.70; 9.25; 9.60; 9.95; 10.50; 10.85; 11.50; 12.10; 13.85; 14.90µ.

$\delta D_2O$: 1.00–1.43 m(6H); 1.70 m(3H); 1.93 m(3H); 3.20–4.20 m(8H); 5.65 m(1H); 6.65–7.15 m(3H) ppm.

EXAMPLE 5

Ethoxyquin (230 g) and 2,3,4,6-tetra-O-acetyl-α-D-galactopyranosyl bromide (218 g) were stirred together at 80° for 17 hours. Acetone (400 ml) was added to the hot reaction mixture and stirring was continued for an additional 20 minutes. After cooling the precipitated ethoxyquin-hydrobromide was filtered off, washed with acetone and the filtrate was evaporated to dryness under reduced pressure.

The crude product was recrystallized (isopropanol) yielding 123.0 g of a white, crystalline product being 1-(2,3,4,6-tetra-O-acetyl-D-galactopyranosyl)-6-ethoxy-1,2-dihydro-2,2,4-trimethylquinoline, m.p. 150°–151°.

$v_{max}^{KBr}$: 3.40; 5.70; 6.05; 6.20; 6.35; 6.70; 7.00; 7.30; 7.70; 8.20; 9.00; 9.20; 9.50; 9.85; 10.40; 10.55; 10.90; 11.40; 12.15; 12.40; 13.00; 13.55; 13.70; 14.00; 14.95µ.

$\delta CDCl_3$: 1.10 s(3H); 1.37 t(J=7Hz; 3H); 1.41 s(3H); 1.85 s(3H); 1.98 s(6H); 2.14 s(3H); 2.23 s(3H); 3.75–4.40 m, 4.65–6.00 m(10H); 6.55–6.83 m(2H); 7.30–7.65 m(1H) ppm.

EXAMPLE 6

$NaOCH_3$ (2,2M, 0.5 ml) was added at room temperature to a stirred solution of 1-(2,3,4,6-tetra-O-acetyl-D-galactopyranosyl)-6-ethoxy-1,2-dihydro-2,2,4-trimethylquinoline (50 g) in abs. MeOH (50 ml). After 1 hour the solution was neutralized (glacial HOAc). The solution was filtered and the filtrate was evaporated to dryness under reduced pressure. The crystalline product was recrystallized from ethanol, yielding 2.9 g of 1-D-glactopyranosyl-6-ethoxy-1,2-dihydro-2,2,4-trimethylquinoline (hereinafter called "ethoxyquin-galactoside"). mp: 162°–163°.

$v_{max}^{KBr}$: 3.00; 3.40; 6.35; 6.70; 7.00; 7.10; 7.20; 7.35; 7.45; 7.60; 7.70; 8.00; 8.35; 8.80; 9.15; 9.30; 9.60; 10.15; 10.60; 10.90; 11.20; 11.55; 11.80; 12.10; 12.75; 13.35; 14.10µ.

δD$_6$-DMSO: 0.8–1.65 m(9H); 1.83 m(3H); 3.00–5.00 m(13H); 5.40 m(1H); 6.30–6.70 m(2H); 7.28–7.65 m(1H) ppm.

EXAMPLE 7

2-Acetamido-3,4,6-tri-O-acetyl-D-glucopyranosyl chloride (18.3 g) and ethoxyquin (22.1 g) were vigorously stirred together at 80° for 3 hours. Acetone (50 ml) was added to the hot reaction mixture and stirring was continued for 0.5 hours. After cooling, the solid ethoxyquin-hydrochloride was filtered, washed with acetone and the combined filtrates were evaporated under reduced pressure. The crude product was purified by column chromatography on silica (ethylacetate-benzene 1:4). 16.5 g of 1-(2-acetamido-3,4,6-tri-O-acetyl-2-deoxy-D-glucopyranosyl)-6-ethoxy-1,2-dihydro-2,2,4-trimethylquinoline were obtained. Analytical grade sample was obtained by recrystallisation from ether or isopropanol. m.p. 186°–187°.

$v_{max}^{KBr}$: 3.00; 3.20; 3.30; 5.65; 5.95; 6.30; 6.65; 6.95; 7.25; 7.65; 8.05; 8.65; 8.85; 9.10; 9.55; 10.00; 10.50; 10.80; 11.25; 11.70; 11.90; 12.25; 12.80; 13.30; 13.65; 14.90μ.

δCDCl$_3$: 1.08 s(3H); 1.25–1.55 m(6H); 1.55 s(3H); 1.85–2.18 m(12H); 3.65–4.38 m(6H); 4.88–5.92 m(5H); 6.60–6.85 m(2H); 7.15–7.45 m(1H) ppm.

EXAMPLE 8

To a solution of 1-(2-acetamide-3,4,6-tri-O-acetyl-D-glucopyranosyl)-6-ethoxy-1,2-dihydro-2,2,4-trimethylquinoline (5.0 g) in abs.CH$_3$OH (150 ml), NaOCH$_3$(2.2 M, 0.5 ml) was added. The solution was stirred at room temperature for 2 hours and then neutralized with Amberlite-IR-120 (H+). The resin was filtered off and the filtrate was evaporated to dryness under reduced pressure, yielding 3.85 g of a white, amorphous solid being 1-(2-acetamido-2-deoxy-D-glucopyranosyl)-6-ethoxy-1,2-dihydro-2,2,4-trimethylquinoline. Recrystallisation from ethanol-ether or ethanol-ethylacetate. m.p.: 114.5°–116°.

$v_{max}^{KBr}$: 3.00; 3.40; 6.05; 6.40; 6.70; 6.95; 7.25; 7.70; 7.95; 8.30; 8.45; 8.55; 8.70; 9.00; 9.30; 9.55; 10.00; 10.45; 10.70; 11.20; 11.55; 11.75; 12.35; 13.00; 13.45; 13.80μ.

δCDCl$_3$: 0.90–2.15 m(15H); 3.15–4.25 m(9H); 4.60–4.95 m(1H); (+D$_2$O) 5.45 m(1H); 6.68 m(2H); 7.25 m(1H) ppm.

EXAMPLE 9

2,3,4-Tri-O-acetyl-α-D-xylopyranosyl bromide (18.8 g) and ethoxyquin (29.2 g) were stirred together at 70° for 6 hours. Acetone (100 ml) was added to the hot solution and stirring continued for 15 minutes. After cooling, the ethoxyquinhydrobromide was filtered off, washed with acetone and the combined filtrates were evaporated to dryness under reduced pressure yielding brown syrup (35.3 g). Part of the crude reaction product (12.5 g) was purified by column chromatography on silica (ethylacetate-benzene (1:9) and 5.9 g of 1-(2,3,4-tri-O-acetyl-D-xylopyranosyl)-6-ethoxy-1,2-dihydro-2,2,4-trimethylquinoline, was obtained as a highly viscous syrup, which crystallised from isopropanol. m.p. 71°–72°.

$v_{max}^{KBr}$: 3.35; 3.65; 6.15; 6.30; 6.65; 6.95; 7.30; 7.50; 8.15; 8.65; 8.95; 9.50; 10.15; 10.40; 10.65; 10.95; 11.40; 11.65; 11.95; 12.10; 12.25; 12.70; 12.90; 13.35; 13.70; 13.95; 14.50; 14.90μ.

δCDCl$_3$: 1.10 s(3H); 1.37 t(J=7.0H); 1.42 s(6H); 1.78 s(3H); 1.95 s(6H); 2.03 s(3H); 3.15–3.55 m(1H); 3.75–4.35 m(3H); 4.60–5.60 m(5H); 6.58–6.68 m(2H); 7.20–7.50 m(1H) ppm.

EXAMPLE 10

To a solution of 1-(2,3,4-tri-6-acetyl-D-xylopyranosyl)-6-ethoxy-1,2-dihydro-2,2,4-trimethylquinoline (3.2 g) in abs. CH$_3$OH (25 ml), NaOCH$_3$ (2,2 M, 0.3 ml) was added. The reaction mixture was stirred at room temperature for 10 minutes, then neutralised (Amberlite IR-120 H+), filtered and the filtrate was evaporated to dryness under reduced pressure, yielding 1.9 g of 1-D-xylopyranosyl-6-ethoxy-1,2-dihydro-2,2,4-trimethylquinoline as white amorphous solid.

$v_{max}^{KBr}$: 2.95; 3.40; 6.20; 6.35; 6.70; 6.95; 7.20; 7.35; 7.60; 7.90; 8.25; 8.45; 8.50; 8.70; 8.95; 9.15; 9.50; 10.15; 10.50; 11.10; 11.45; 11.65; 12.30; 12.95; 13.35; 13.70; 14.90μ.

δCDCl$_3$: 0.95–1.53 m(9H); 1.95 m(3H); 2.80–4.60 m(11H); 5.45 m(1H); 6.50–6.80 m(2H); 7.10–7.38 (1H) ppm.

EXAMPLE 11

A solution of ethoxyquin (30 g) in ethylacetate (300 ml) was added dropwise at room temperature to a stirred saturated solution of phosgene in ethylacetate (100 ml). Phosgene was rapidly and continuously bubbled into the stirred solution during the period of addition (2 hours). After the addition of the ethoxyquin solution was finished, phosgene bubbling was stopped and the solvent was gradually distilled (atmospheric pressure). At the end of the distillation, CCl$_4$ (50 ml) was added and distillation continued under a slow stream of N$_2$ (to eliminate traces of phosgene), another portion of CCl$_4$ (50 ml) was added. Undesired ethoxyquin hydrochloride was filtered off (9.26 g), and the filtrate was evaporated to dryness under reduced pressure, yielding 1-Chlorocarbonyl-6-ethoxy-1,2-dihydro-2,2,4-trimethylquinoline as yellow, viscous syrup, which crystallised on standing (31.67 g). Recrystallisation from acetone. m.p.: 75.5°–76.5°.

$v_{max}^{KBr}$: 3.40; 5.70; 6.25; 6.70; 6.85; 7.05; 7.20; 7.40; 7.60; 7.70; 7.90; 8.30; 8.65; 8.85; 9.00; 9.40; 9.55; 9.90; 10.25; 10.40; 10.50; 10.65; 10.80; 11.30; 11.50; 11.70; 12.10; 12.80; 13.60; 14.05; 15.00μ.

δCDCl$_3$: 1.47 t(J=7 Hz: 3H); 1.53 s(6H); 2.08 d(J=1.5H); 4.11 quartet(J=7 Hz); 5.68 dm (J=1.5 Hz); 6.70–6.95 m(2H); 7.18–7.39 m(1H) ppm.

EXAMPLE 12

A mixture of 1,2,3,4-di-O-isopropylidene-D-glactopyranose (1.3 g) and 1-chlorocarbonyl-6-ethoxy-1,2-dihydro-2,2,4-trimethylquinoline (1.4 g) was heated (70°–80°) with stirring in the presence of anhydrous K$_2$CO$_3$ (140 mg) for 40 minutes. After cooling, CHCl$_3$ (45 ml) was added and the solution was filtered, washed with saturated aqueous NaHCO$_3$ and H$_2$O, dried over anhydrous Na$_2$SO$_4$, filtered and the filtrate was evaporated to dryness under reduced pressure. The crude product was purified on silica column (ethylacetate-benzene 1:9), yielding 2.0 g of 1-(1,2,3,4-di-O-isopropylidene-6-D-galactopyranosyloxycarbonyl)-6-ethoxy-1,2-dihydro-2,2,4-trimethylquinoline as a highly viscous syrup (crystallises on standing). Recrystallisation from methanol.

m.p.: 124°–126°.

$v_{max}^{KBr}$: 3.40; 5.90; 6.20; 6.35; 6.70; 6.90; 7.00; 7.10; 7.25; 7.40; 7.55; 7.60; 7.75; 8.00; 8.30; 8.60; 8.95; 9.20;

9.40; 9.95; 10.20; 10.30; 10.50; 10.65; 10.90; 11.20; 11.55; 12.25; 12.40; 12.95; 13.15; 13.60; 14.40; 15.00μ.

$\delta CDCl_3$: 1.25–1.58 m(21H); 1.95 m(3H); 3.75–4.70 m(8H); 5.42–5.65 m(2H); 6.55–6.82 m(2H); 7.18–7.42 m(1H) ppm.

EXAMPLE 13

1-(1,2,3,4-Di-O-isopropylidene-D-galactopyranosyloxycarbonyl)-6-ethoxy-1,2-dihydro-2,2,4-trimethylquinoline (1.47 g) was dissolved in 90% trifluoroacetic acid-H$_2$O (14.7 ml) with stirring. The solution was kept at room temperature for 10 minutes, then evaporated to dryness under reduced pressure. The crude product was purified in silica column (acetone-benzene 3:2), yielding 1.0 g of a pure 1-(6-D-galactopyranosyloxycarbonyl)-6-ethoxy-1,2-dihydro-2,2,4-trimethylquinoline as a white, amorphous solid.

$v_{max}^{KBr}$: 2.95; 3.35; 5.90; 6.20; 6.30; 6.95; 7.20; 7.40; 7.75; 8.00; 8.25; 8.50; 8.75; 9.20; 10.40; 10.75; 11.50; 12.35; 13.10; 13.80; 14.90μ.

$\delta CDCl_3$: 1.13–1.50 m(9H); 1.83 m(3H); 3.43–4.60 m(9H); 5.43 m(1H); 6.48–6.75 m(2H); 6.90–7.20 m(1H) ppm. (+D$_2$O)

EXAMPLE 14

1-Chlorocarbonyl-6-ethoxy-1,2-dihydro-2,2,4-trimethylquinoline (3.47 g) and anhydrous K$_2$CO$_3$ (1.7 g) were added to a stirred melt (140°) of 1,2,3,4-tetra-O-acetyl-β-D-glucopyranose (5.0 g). A second amount of the chlorocarbonyl derivative (3.47 g) and anhydrous K$_2$CO$_3$ (1.7 g) was added after 10 minutes from the first addition. The heating was stopped after a total period of 20 minutes. After cooling ether was added and the solution was filtered and evaporated. The crude product was purified on a silica column (ethylacetate-benzene 1:9), yielding 6.6 g of 1-(1,2,3,4-tetra-O-acetyl-6-D-glucopyranosyloxycarbonyl)6-ethoxy-1,2-dihydro-2,2,4-trimethylquinoline as a highly viscous syrup which slowly crystallised on standing. Recrystallisation from isopropanol or hexane.

m.p.: 123°–125°.

$v_{max}^{KBr}$: 3.40; 5.75; 5.90; 6.25; 6.75; 7.05; 7.35; 7.55; 7.65; 7.80; 8.10; 8.30; 8.60; 8.95; 9.25; 9.40; 9.70; 10.25; 10.50; 10.95; 11.15; 11.75; 12.05; 12.40; 13.25; 14.30μ.

$\delta CDCl_3$: 1.40 t(J=7 Hz:3H); 1.45 s(6H); 2.00 m, 2.10 s(15H); 3.83–4.28 m(5H); 4.78–5.80 m(5H); 6.63–6.83 m(2H); 7.03–7.23 m(1H) ppm.

EXAMPLE 15

To a solution of 1-(1,2,3,4-tetra-O-acetyl-6-D-glucopyranosyloxycarbonyl)-6-ethoxy-1,2-dihydro-2,2,4-trimethylquinoline (1.0 g) in absolute CH$_3$OH (50 ml), 2,2 M NaOCH$_3$(0.5 ml) was added, and the solution was kept at room temperature for 5 minutes. After neutralization (Amberlite IR-120 H$^+$) and filtration, the resulted solution was treated with active charcoal, filtered and evaporated to dryness under reduced pressure, yielding 0.56 g of 1-(6-D-glucopyranosyloxycarbonyl)-6-ethoxy-1,2-dihydro-2,2,4-trimethylquinoline as a pure white amorphous solid. Recrystallisation from H$_2$O.

m.p.: 181°–182°

$v_{max}^{KBr}$: 2.95; 3.45; 5.95; 6.25; 6.40; 6.70; 6.80; 6.90; 7.00; 7.20; 7.40; 7.55; 7.75; 7.95; 8.15; 8.30; 8.55; 8.75; 9.00; 9.25; 9.55; 10.10; 10.35; 10.75; 11.00; 11.60; 11.90; 12.20; 13.10; 13.65; 14.45; 14.95μ.

$\delta D_6$-DMSO: 1.20–1.65 m(9H); 2.03 m(3H); 2.90–5.25 m(13H); 5.65 m(1H); 6.65–6.98 m(2H); 7.15–7.43 m(1H) ppm.

EXAMPLE 16

1-Chlorocarbonyl-6-ethoxy-1,2-dihydro-2,2,4-trimethylquinoline (2.8 g) was dissolved with stirring in abs. methanol (10 ml). Stirring continued at room temperature for 1 hour. The solution was then treated with active charcoal, filtered and evaporated to dryness, yielding colourless, oily material which crystallized on standing. Pure 1-carbomethoxy-6-ethoxy-1,2-dihydro2,2,4-trimethylquinoline (2.2 g) was obtained by recrystallisation from methanol.

m.p.: 54.5°–56.5° (methanol).

$\delta CDCl_3$: 1.41 t(J=7.0 Hz), 1.50 s(9H); 2.00 d(J=1.5 Hz; 3H); 3.70 s(3H); 4.08 quartet (J=7.0 Hz 2H); 5.54 dm (J=1.5 Hz; 1H); 6.62–7.48 m(3H) ppm.

$v_{max}^{KBr}$: 3.30; 3.39; 5.87; 6.19; 6.35; 6.69; 6.73; 6.92; 7.18; 7.38; 7.51; 7.70; 7.95; 8.30; 8.36; 8.52; 8.67; 8.95; 9.15; 9.39; 9.49; 9.90; 10.10; 10.35; 10.60; 10.70; 11.40; 11.60; 12.30; 12.70; 13.10; 13.60; 15.70μ.

EXAMPLE 17

2,3,4,6-Tetra-O-acetyl-β-D-glucose (5.0 g) was heated with stirring to 140°. A well-mixed mixture of 1-chlorocarbonyl-6-ethoxy1,2-dihydro-2,2,4-trimethylquinoline (4.0 g) and of anhydrous K$_2$CO$_3$ (2.0 g) was added to the molten glucose derivative under a slow stream of nitrogen. Another quantity of well-mixed chlorocarbonyl derivative (4.0 g) and of anhydrous K$_2$CO$_3$(2.0 g) was added to the hot reaction mixture 5 minutes after the end of the first addition. Heating, stirring and the nitrogen flow were continued for 20 minutes. The reaction mixture was then cooled to room temperature. The dark, viscous syrup obtained was dissolved in CHCl$_3$, filtered and evaporated to dryness under reduced pressure. The syrup obtained was chromatographed on a silica column (benzene-ethylacetate 9:1). The desired product, 1-(2,3,4,6-tetra-O-acetyl-1-D-glucopyranoxyloxycarbonyl)-6-ethoxy-1,2-dihydro-2,2,4-trimethylquinoline, was isolated in almost pure form (TLC) (4.4 g). It was identified according to its IR spectrum ($v_{max}^{NaCl}$: 3.22; 3.25; 3.29; 5.70; 5.81μ. Sodium methylate (2.2 ml, 0.5 ml) was added to a solution of said trimethylquinoline (2.2 g) in abs. methanol (50 ml). The solution was kept at room temperature for 20 minutes and then neutralized (Amberlite IR-120 (H$^+$)). The resin was filtered off and the filtrate was evaporated to dryness under reduced pressure, leaving almost pure 1-(1-D-glucopyranosyloxycarbonyl)-6-ethoxy-1,2-dihydro-2,2,4-trimethylquinoline (1.5 g).

m.p.: 98°–101° dioxane-hexane $v_{max}^{KBr}$: 3.02; 3.28; 3.30; 3.36; 3.40; 3.46; 3.50; 5.82; 6.20; 6.35; 6.70; 6.75; 6.84; 6.96; 7.08; 7.18; 7.21; 7.38; 7.48; 7.58; 7.71; 7.79; 7.87; 7.93; 7.98; 8.12; 8.52; 8.70; 8.96; 9.18; 9.50; 9.78; 9.96; 10.20; 10.40; 10.70; 11.10; 11.30; 11.50; 11.70; 12.00; 12.20; 12.40; 13.20; 13.60; 14.10; 15.70μ.

EXAMPLE 18

Dry ammonia was passed for 15 minutes through a solution of 1-chlorocarbonyl-6-ethoxy-1,2-dihydro-2,2,4-trimethylquinoline (1.5 g) in benzene (15 ml) and ethanol (6 ml). The ammonium chloride was filtered and the filtrate was evaporated to dryness under reduced pressure. Addition of hexane caused the precipitation of 1-carboxamido-6-ethoxy-1,2-dihydro-2,2,4- trimethylquinoline (620 mg) as white, crystalline material (hereinafter called "ethoxyquin ureide").

m.p.: 114.5°–115° (cyclohexane).

$\nu_{max}^{CHCl_3}$: 2.72; 2.82; 2.92; 3.35; 3.41; 3.48; 5.98; 6.22; 6.32; 6.71; 6.78; 6.88; 6.99; 7.21; 7.30; 7.77; 7.81; 7.89; 8.35; 8.56; 8.91; 9.10; 9.50; 9.90; 10.30; 10.90; 10.80; 11.50; 11.70; 15.80μ.

$\delta CCl_4$: 1.38 t(J=7.0 Hz; 3H); 1.43 s(6H); 1.95 d(J=1.5 Hz;3H); 3.93 quartet (J=7.0 Hz;2H); 5.40 d(J=1.5 Hz;1H); 5.63 m (2H); 6.40–6.70 m(2H); 6.95–7.28 m(1H) ppm.

EXAMPLE 19

$PCl_5$ (6.7 g) was added to a stirred, ice-cooled suspension of Carbobenzoxyglycine (6.3 g) in dry ether (35 ml). Stirring was continued until all the solid dissolved. The suspension was filtered, the filtrate cooled in an ice bath and ethoxyquin (19.6 g) was added. Stirring was continued for 15 hours. Ethoxyquin hydrochloride obtained was filtered off, and the volume of the solvent was decreased under reduced pressure, causing the precipitation of 1-carbobenzoxyglycyl-6-ethoxy-1,2-dihydro-2,2,4-trimethylquinoline (8.8 g); m.p.: 112°–113° (isoproponol).

$\nu_{max}^{KBr}$: 3.05; 3.25; 3.35; 5.80; 6.05; 6.20; 6.45; 6.70; 6.85; 6.95; 7.05; 7.20; 7.60; 7.95; 8.10; 8.55; 9.00; 9.50; 9.90; 10.40; 10.60; 10.80; 11.00; 11.45; 11.75; 12.05; 12.40; 12.50; 13.40; 13.50; 14.35;μ.

$\delta CDCl_3$: 1.40 t(J=7.0 Hz); 1.45 s(9 Hz); 1.95 d(J=1.5 Hz; 3H); 3.68–4.25 m(4H); 5.05 s(2H); 5.55 m(2H); 6.48–7.48 m(8H) ppm.

EXAMPLE 20

$PCl_5$ (3.9 g) was added to a stirred suspension of carbobenzoxy-β-alanine (3.9 g) in dry ether (18 ml) at −10°. Stirring was continued until all the solid had dissolved. The solution was filtered, the filtrate was cooled in an icebath, and ethoxyquin (11.5 g) was added. Stirring was continued for 15 hours. Ethoxyquin hydrochloride formed was filtered off and the filtrate was then evaporated to dryness. The viscous, oily material obtained was chromatographed on a silica column. The desired products, 1-(carbobenzoxy-β-alanyl)-6-ethoxy-1,2-dihydro-2,2,4-trimethylquinoline (4.0 g) was eluted from the column with benzene-ethylacetate (9:1 V/V).

m.p.: 68°–70° (hexane).

$\nu_{max}^{KBr}$: 3.00; 3.22–3.32; 3.35; 3.38; 3.48; 5.82; 6.11; 6.45; 6.58; 6.62; 6.72; 6.74; 6.85; 6.98; 7.09; 7.23; 7.47; 7.58; 7.79; 8.08; 8.30; 8.61; 8.80; 8.98; 9.30; 9.55; 9.80; 10.60; 10.80; 10.90; 11.20; 11.50; 11.80; 12.10; 12.40; 12.80; 13.40; 14.30; 15.70μ.

$\delta CDCl_3$: 1.40 t(J=7.0 Hz), 1.46 s(9H); 1.96 d(J=1.5 Hz; 3H); 2.55 dd(J=6.0 Hz;2H); 3.40 dm(J=6.0 Hz; 2H); 4.00 quartet (J=7.0 Hz;2H); 5.00s (2H); 5.48 dm(J=1.5 Hz; 1H); 6.66 m(3H); 7.26 s(5H)ppm.

EXAMPLE 21

A mixture of 1-(carbobenzoxyglycyl)-6-ethoxy-1,2-dihydro-2,2,4-trimethylquinoline (0.40 g) dissolved in methanol (10 ml), cyclohexene (0.1 ml) and 10% Pd/C (0.4 g) was heated to reflux with stirring for 15 minutes. After cooling to room temperature, the catalyst was filtered off and the filtrate was evaporated to dryness under reduced pressure, leaving a viscous, oily material (0.22 g). The desired product, 1-glycyl-6-ethoxy-1,2-dihydro-2,2,4-trimethylquinoline, a colourless, highly viscous oily compound, was purified by column chromatography (silica, benzene-acetone 2:3).

$\nu_{max}^{NaCl}$: 2.97; 3.02; 3.36; 3.41; 3.48; 6.02; 6.22; 6.35; 6.71; 6.97; 7.21; 7.37; 7.71; 7.91; 8.10; 8.30; 8.65; 8.98; 9.20; 9.52; 9.90; 10.40; 10.70; 11.50; 11.70; 12.10; 12.40; 13.20; 13.50; 15.60μ.

$\delta CCl_4$: 1.48 t(J=7 Hz), 1.57 s(9H); 2.08 m(3H); 3.36 m(2H); 4.13 m(4H); 5.68 m(1H); 6.88 m(3H) ppm.

EXAMPLE 22

1-(Carbobenzoxyglycyl)-6-ethoxy-1,2-dihydro-2,2,4-trimethylquinoline (1.0 g) was dissolved in a 45% $HBr/CH_3COOH$ solution (which had been treated with few phenol crystals before use). The solution was kept at room temperature for 30 minutes. Ether (20 ml) was then added, causing the precipitation of a yellow gum. The gum was dissolved in water (20 ml) and the solution was neutralized with $NaHCO_3$. The mixture was extracted with ether (3×10 ml), the etheral solution was dried ($Na_2SO_4$), filtered and the filtrate evaporated to dryness under reduced pressure, leaving a pale-yellow oily material (0.43 g). A pure product was obtained by column chromatography (silica, benzene-acetone 2:3), which was identical (according to TLC, IR and NdMR) with the 1-glycyl-6-ethoxy-1,2-dihydro-2,2,4-trimethylquinoline obtained in Example 21.

EXAMPLE 23

A solution of 1-(carbobenzoxyglycyl)-6-ethoxy-1,2-dihydro2,2,4-trimethylquinoline (1.0 g), L-tartaric acid (0.55 g) and cyclohexene (0.3 ml) in methanol (25 ml) was heated to reflux with stirring in the presence of 10% Pd/C (1.0 g) for 15 minutes. The catalyst was filtered off after cooling, and the filtrate was evaporated to dryness under reduced pressure. The obtained material crystallized after being treated with isopropanol. The white, crystalline material (0.9 g) was recrystallized from water, and identified as the tartarate salt of the product obtained in Examples 21 and 22.

m.p.: 136°–137°.

$\nu_{max}^{KBr}$: 2.88; 3.00; 3.05; 3.35; 3.39; 3.44; 5.78; 5.97; 6.22; 6.70; 6.79; 7.01; 7.20; 7.39; 7.51; 7.68; 7.84; 8.02; 8.23; 8.59; 8.80; 8.98; 9.28; 9.33; 9.55; 9.90; 10.20; 10.40; 10.70; 11.10; 11.40; 11.60; 11.80; 12.00; 12.20; 12.70; 13.30; 14.70; 15.50μ.

EXAMPLE 24

Example 21 was precisely repeated with 1-(carbobenzoxy-β-alanyl)-6-ethoxy-1,2-dihydro-2,2,4-trimethylquinoline as starting material. The purified product, a pale-yellow oily material, was identified as 1-(β-alanyl)-6-ethoxy-1,2-dihydro-2,2,4-trimethylquinoline.

$\nu_{max}^{NaCl}$: 2.98; 3.03; 3.31; 3.37; 3.42; 3.49; 6.05; 6.21; 6.35; 6.71; 6.87; 6.97; 7.21; 7.36; 7.72; 7.89; 8.11; 8.30; 8.60; 9.00; 9.30; 9.52; 9.90; 10.80; 11.50; 12.30; 13.20; 13.50μ.

$ccl_4$: 1.50 t(J=7.0 Hz), 1.57 s(9H); 2.08 m(3H); 2.60 dd (J=6.0 Hz; 2H); 3.03 m(4H); 4.10 quartet (J=7.0 Hz;2H); 5.60 m(1H); 6.81 m(3H) ppm.

EXAMPLE 25

Example 23 was repeated with 1-(carbobenzoxy-β-alanyl)-6-ethoxy-1,2-dihydro-2,2,4-trimethylquinoline (3.0 g), L-tartaric acid (1.6 g), cyclohexene (0.6 ml),$CH_3OH$ (60 ml) and 5% Pd/C (3.0 g). The white, crystalline product, (3.0 g) the tartarate salt of 1-(β-alanyl)-6-ethoxy-1,2-dihydro-2,2,4-trimethylquinoline obtained, was recrystallised from $H_2O$.

m.p.: 157°–158°.

$\nu_{max}{}^{KBr}$: 2.88; 2.97; 3.17; 3.37; 3.42; 3.47; 3.49; 5.79; 6.08; 6.17; 6.38; 6.70; 6.89; 7.00; 7.09; 7.18; 7.31; 7.40; 7.70; 7.86; 7.98; 8.10; 8.22; 8.55; 8.81; 8.99; 9.32; 9.57; 10.20; 10.40; 10.70; 11.10; 11.40; 11.50; 11.70; 11.80; 12.10; 12.20; 12.70; 13.00; 13.40; 13.70; 14.70; 15.20; 15.60μ.

EXAMPLE 26

A mixture of methyl (tri-O-acetyl-D-glycopyranosyl-bromide)uronate (4.9 g) and ethoxyquin (5.4 g) was heated to 80° and stirred together for 12 hours. Acetone (40 ml) was added and the ethoxyquin-hydrobromide obtained was filtered off. The filtrate was evaporated to dryness under reduced pressure. The crude product was purified on a silica column, (benzene-ethylacetate 18:1) to yield 4.0 g of 1-(methyl tri-O-acetyl-D-glucopyranosylurono)-6-ethoxy-1,2-dihydro-2,2,4-trimethylquinoline; m.p.: 122.5°–123° (methanol).

$\nu_{max}{}^{KBr}$: 3.35; 5.65; 6.15; 6.30; 6.65; 6.75; 6.95; 7.00; 7.20; 7.45; 8.05; 8.15; 8.80; 9.05; 9.40; 9.55; 9.65; 9.80; 10.20; 10.75; 11.05; 11.25; 11.45; 11.65; 12.40; 12.70; 13.50; 13.70; 14.70; 14.95μ.

$\delta CDCl_3$: 1.10 s(3H); 1.38 t(J=7.0H), 1.41 s(6H); 1.78 s(3H); 1.85–2.13 m(9H); 3.75 s(3H); 3.80–4.23 m, 4.68–5.53 m (8H); 6.60–6.85 m(2H); 7.20–7.48 (1H) ppm.

EXAMPLE 27

2.2 M $NaOCH_3$ (0.4 ml) was added to a solution of 1-(methyltri-O-acetyl-D-glucopyranosylurono)-6-ethoxy-1,2-dihydro-2,2,4-trimethylquinoline (1.0 g) in abs. methanol (50 ml). The solution obtained was stirred for 1 hour at room temperature, then neutralized with Amberlite IR-120(H+). The resin was filtered off, the filtrate was treated with active charcoal, filtered and evaporated under reduced pressure, yielding 1-(methyl-D-glucopyranosylurono)-6-ethoxy-1,2-dihydro-2,2,4-trimethylquinoline as colourless, amorphous solid (0.62 g).

$\nu_{max}{}^{KBr}$: 2.90; 3.10; 3.35; 5.70; 6.20; 6.35; 6.75; 6.85; 6.95; 7.20; 7.35; 7.45; 7.75; 7.90; 8.05; 8.30; 8.40; 8.70; 9.10; 9.20; 9.55; 9.80; 9.95; 10.10; 10.30; 10.70; 11.10; 11.50; 11.60; 12.30; 12.80; 13.45; 13.75; 14.20; 16.0μ.

$\delta D_6 DMSO$: 1.00–1.55 m(9H); 1.95 m(3H); 3.75, 3.10–4.25 m, 4.40–4.75 m; 4.90–5.43 m(13H); 5.50 m(1H); 6.48–6.85 m (2H); 7.13–7.45 m(1H) ppm.

EXAMPLE 28

1-(Methyl tri-O-acetyl-D-glucopyranosylurono)-6-ethoxy-1,2-dihydro-2,2,4-trimethylquinoline (0.5 g) was dissolved in abs. methanol (50 ml) saturated with ammonia. The solution obtained was kept for 18 hours at 8°. Then it was evaporated to dryness under reduced pressure. The residue was dissolved in methanol and the solution obtained was treated with active charcoal, filtered and evaporated to dryness to yield 1-(D-glucopyranoxyluronamido)-6-ethoxy-1,2-dihydro-2,2,4-trimethylquinoline as colourless solid. m.p.: 114°–115°.

$\nu_{max}{}^{KBr}$: 2.90–3.05; 3.35; 3.40; 3.50; 5.95; 6.20; 6.35; 6.75; 7.00; 7.05; 7.20; 7.35; 7.80; 8.25; 8.55; 8.70; 9.00; 9.20; 9.50; 9.85; 10.30; 11.00; 11.50; 11.60; 12.30; 13.00; 13.45μ.

$\delta CDCl_3$: 1.05–1.53 m(9H); 1.95 m(3H); 2.75–5.00 m(12H); 5.55 m(1H); 6.32–6.75 m(2H); 7.05–7.35 m(1H) ppm.

EXAMPLE 29

A stirred mixture of 2,3,4,5-tetra-O-acetyl-D-galactaroyl dichloride (1.7 g) and of ethoxyquin (3.56 g) was heated at 120° for 3 hours. The resulting mixture was suspended in hot acetone and the precipitating solid (ethoxyquin hydrochloride) was filtered off. The filtrate was then evaporated to dryness under reduced pressure. The crude reaction product was chromatographed on a silica column (benzene-ethylacetate 9:1), yielding 0.65 g of di-(6-ethoxy-1,2-dihydro-2,2,4-trimethyl-1-quinolyl)-amido-2,3,4,5-tetra-O-acetylglactaric acid; m.p. 254.5°–255.5° (acetone).

$\nu_{max}{}^{KBr}$: 3.32; 3.37. 3.40; 3.48; 5.72; 5.92; 6.23; 6.68; 6.77; 6.88; 7.00; 7.27; 7.52; 7.72; 7.83; 7.94; 8.09; 8.26; 8.59; 8.83; 8.97; 9.08; 9.48; 9.58; 9.90; 10.20; 10.50; 10.80; 11.50; 11.75; 11.85; 12.00; 12.20; 13.45; 13.80; 15.15; 15.55μ.

$\delta CDCl_3$: 1.00–2.20 m(36H); 4.10 quartet (J=7.0 Hz; 4H); 4.82 s(2H); 5.60 m(2H); 5.67 s(2H); 6.60–6.97 m(4H); 7.30–7.57 m(2H) ppm.

EXAMPLE 30

Ethoxyquin glucoside (5 g) is dissolved in propylene glycol (95 g) by mixing under sterile conditions, to yield a solution which can be used for injections.

EXAMPLE 31

A mixture comprising:
Ethoxyquin galactoside: 5.0 g
Lactose: 15.0 g
Soyabean meal: 80.0 g
is admixed thoroughly in a Fisher-Kendall mixer to yield a mixture which can be utilized as a premix for animal feedstuffs.

EXAMPLE 32

Ethoxyquin galactoside (50 parts) and Lactose U.S.P. grade (200 parts) are granulated together with a 10% solution of Polyvinylpyrrolidone (PVP)-K30 in isopropanol. To the dried and sifted granulate, 5% of dry starch and 0.3% of Magnesium Stearate are added and well mixed. The whole mass is compressed to tablets each weighing about 0.265 g and each containing 50 mg of ethoxyquin galactoside.

In the following Examples the activity of some of the compounds of general formula I is illustrated. Albino mice were used in all examples. The mice of group A received a low Vitamin E concentration diet (8 ppm) for 6 weeks starting 12 days after birth. This treatment caused a remarkable Vitamin E deficiency and a considerably increased sensitivity to iron poisoning. Group B mice received the regular commercial food (Vit. E conc. 150 ppm). Both groups of mice were of the same age.

EXAMPLE 33

Fifteen Vitamin E deficient mice (Vitamin E blood level 0.2 mg %) of group A and 20 regularly fed mice (Vitamin E blood level 1.4 mg %) of group B were injected i.p. with a 10% solution of an Iron Dextran complex at a level of 1000 mg Fe/Kg body weight. The mortality observed after 5 days in group A was 14/15 and in group B 1/20.

EXAMPLE 34

Eight Vitamin E-deficient mice were injected s.c. with a 20% solution of ethoxyquin-glucoside in propyleneglycol at a level of 200 mg/kg body weight. A 10% solution of the Iron-Dextran complex was immediately injected i.p. at a level of 1000 mg/kg body weight. The mortality observed after 5 days was 1/8.

EXAMPLE 35

Example 34 was repeated exactly but the ethoxyquin-glucoside solution was injected s.c., at a level of 400 mg/kg body weight, on 10 mice. The mortality observed after 5 days was 0/10.

EXAMPLE 36

A mixture of a 10% iron-dextran solution and 20% solution of the ethoxyquin-glucoside in propyleneglycol was prepared and injected i.p. to 8 Vitamin E-deficient mice at a level of 1000 mg of Fe and 200 mg of glucoside/Kg body weight. The mortality observed after 5 days was 1/8.

EXAMPLE 37

Example 34 was repeated, but ethoxyquin-galactoside was used instead of ethoxyquin-glucoside. The mortality observed after 5 days was 2/8.

EXAMPLE 38

Example 34 was repeated on nine mice, but 1-(2-acetamido-3,4,6-tri-O-acetyl-D-glucopyranosyl)-6-ethoxy-1,2-dihydro-2,2,4-trimethylquinoline in dimethyl sulfoxide (DMSO) was used in a level of 250 mg/kg body weight instead of ethoxyquin-glucoside in propylene glycol. The mortality observed after 5 days was 2/9.

EXAMPLE 39

Example 36 was repeated, but 1-(2-acetamido-D-glucopyranosyl)-6-ethoxy-1,2-dihydro-2,2,4-trimethyl-quinoline was used instead of ethoxyquine-glucoside. The mortality observed after 5 days was 1/8.

EXAMPLE 40

Example 36 was repeated on 10 mice, but 1-D-xylopyranosyl-6-ethoxy-1,2-dihydro-2,2,4-trimethyl-quinoline was used instead of ethoxyquin-glucoside. The mortality observed after 5 days was 1/10.

EXAMPLE 41

A finely powdered dry mixture of iron-dextran powder (3.3 g) containing 30% of Fe, ethoxyquin-glucoside (0.2 g) and NaCl (0.1 g) was dissolved with good shaking in water for injection, to yield 10 ml of solution. The solution prepared in this way was injected i.p. to 9 Vitamin E-deficient mice at a level of 100 mg of Fe and 200 mg of ethoxyquin-glucoside/kg body weight. The mortality observed after 5 days was 0/9.

EXAMPLE 42

Eight Vitamin E deficient mice received a daily s.c. injection of ethoxyquin ureide for three consecutive days. The doses per injection were equivalent to 100 mg of ethoxyquin/Kg animal weight. The compound tested was dissolved in propylene glycol, so as to provide the required dose by injecting 0.1 ml of the solution per 10 g body weight. Iron Dextran solution (1000 mg Fe/Kg body weight) was injected i.p. together with the last injection of ethoxyquin ureide. The observed mortality after 5 days was 0.8.

EXAMPLE 43

Example 42 was repeated on eight mice, but ethoxyquin gluconamide pentacetate was used instead of Ethoxyquin ureide. The mortality observed after 5 days was 1/8.

EXAMPLE 44

Finely ground Vitamin E deficient food was homogenously mixed with ethoxyquin ureide and adjusted to a concentration of 0.2% w/w ethoxyquin equivalent.

Two groups (A and B) of eight Vitamin E deficient mice were fed at libitum with the above food. After 3 days of feeding the animals of group A received an i.p. Iron Dextran injection (1000 mg Fe/Kg body weight).

Group B received the same i.p. injection but after seven day feeding.

The animals were observed during 5 consecutive days following the Iron Dextran injections.

The observed mortality was: 0/8 for group A (three day feeding); 0/8 for group B (seven day feeding).

EXAMPLE 45

Example 44 was repeated on two groups of eight mice each, but with ethoxyquin galactoside instead of ethoxyquin ureide.

The observed mortality was: 2/8 for group A (three day feeding); 0/8 for group B (seven day feeding).

EXAMPLE 46

5 ml aliquots of a liver cell suspension in Eagles Minimal Essential Medium (MEM) adjusted to a concentration of $4.10^5$ cell/ml were distributed in three sterile tissue dishes (Falcon). A fourth dish was used for the Blank solution. Ethoxyquin-gluconamide was subsequently added from a 0.2% water solution to all dishes to obtain the following combinations:

| Sample No. | Cell Suspension in MEM | Ethoxyquin gluconamide quantity | Time of incubation |
|---|---|---|---|
| 1 | 5 ml | 400γ | 4 |
| 2 | 5 ml | 200γ | 4 |
| 3 | 5 ml | 200γ | 1 |
| 4 | 5 ml Blank (no cells, only MEM) | 400γ | 4 |

The dishes were incubated at 37° in a $CO_2$ incubator, dish No. 3 for 1 hour, dishes Nos. 1,2 and 4 each for 4 hours. The dishes were then removed from the incubator and the contents centrifugated at 1500 r.p.m. for 5 minutes. The supernatants were extracted with benzene, the benzene extracts were dried and the solvent stripped off in vaccuo. The residues were dissolved in benzene and in the typically fluorescentric extracts of samples 1, 2 and 3, ethoxyquin was detected by TLC. No ethoxyquin gluconamide was found by the mentioned method.

On the other hand, the extract of sample No. 4, treated the same way, showed clearly the presence of ethoxyquin gluconamide but not that of ethoxyquin.

We claim:

1. A compound of the formula:

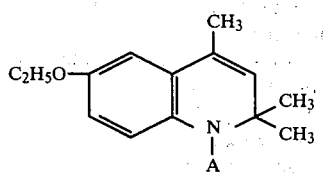

in which A stands for one of the following groups

   I.

B standing for a. (CHOR')$_n$R in which R' stands for H, lower carboxyacyl, or lower alkyl, R stands for CH$_2$OH, carboxyl, or carboxy lower alkyl, or COR''', R''' standing for the ethoxyquin group, and n stands for an integer of 2–6;

b. (CHR'''')$_m$NH$_3$X$^-$ in which R'''' stands for H, or lower alkyl, X$^-$ stands for a non-toxic and physiologically acceptable salt forming anion, and m stands for an integer from 1–6;

c. (CH$_2$)$_m$NR$_1$R$_2$ in which R$_1$, R$_2$ and m have the same meaning as above and R$_2$ in addition can be Cb$_2$;

d. NR'$_1$R'$_2$ in which R'$_1$ and R'$_2$ stands for hydrogen or lower alkyl;

e. OR$_4$ in which R$_4$ stands for lower alkyl, or for

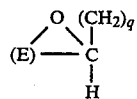

in which E stands for

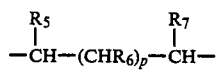

R$_5$, R$_6$ and R$_7$ standing for H, CH$_2$OH, OH, CH$_2$O-lower alkyl, O-lower carboxy acyl, R$_5$ and R$_6$ together standing for

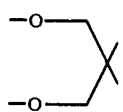

p stands for an integer of 1 or 2, and q stands for an integer of 0 or 1:

   f.

in which E has the same meaning as above; or

   II.

in which E has the same meaning as above, but R$_5$, R$_6$ and R$_7$ may also stand for COHN$_2$.

2. A compound according to claim 1 being 1-(2,3,4,6-tetra-O-acetyl-D-glucopyranosyl)-6-ethoxy-1,2,-dihydro-2,2,4-trimethylquinoline.

3. A compound according to claim 1 being 1-D-glucopyranosyl-6-ethoxy-1,2-dihydro-2,2,4-trimethylquinoline.

4. A compound according to claim 1 being 1-(2,3,4,5,6-penta-O-acetyl-D-gluconyl)-6-ethoxy-1,2-dihydro-2,2,4-trimethylquinoline.

5. A compound according to claim 1 being 1-D-gluconyl-6- ethoxy-1,2-dihydro-2,2,4-trimethylquinoline.

6. A compound according to claim 1 being 1-(2,3,4,6-tetra-O-acetyl-D-galactopyranosyl)-6-ethoxy-1,2-dihydro-2,2,4-trimethylquinoline.

7. A compound according to claim 1 being 1-D-galactopyranosyl-6-ethoxy-1,2-dihydro-1,2-dihydro-2,2,4-trimethylquinoline.

8. A compound according to claim 1 being 1-(2-acetamido-3,4,6-tri-O-acetyl-2-deoxy-D-glucopyranosyl)-6-ethoxy-1,2-dihydro-2,2,4-trimethylquinoline.

9. A compound according to claim 1 being 1-(2-acetamido-2-deoxy-D-glucopyranosyl)-6-ethoxy-1,2-dihydro-2,2,4-trimethylquinoline.

10. A compound according to claim 1 being 1-(2,3,4-tri-O-acetyl-D-xylopyranosyl)-6-ethoxy-1,2-dihydro-2,2,4-trimethylquinoline.

11. A compound according to claim 1 being 1-D-xylopyranosyl-6-ethoxy-1,2-dihydro-2,2,4-trimethylquinoline.

12. A compound according to claim 1 being 1-(1,2,3,4-di-O-isopropylidene-6-D-galactopyranosyloxycarbonyl)-6-ethoxy-1,2-dihydro-2,2,4-trimethylquinoline.

13. 1-(6-D-galactopyranosyloxycarbonyl)-6-ethoxy-1,2-dihydro-2,2,4-trimethylquinoline.

14. 1-(2,3,4,-tetra-O-acetyl-6-D-glucopyranosyloxycarbonyl)-6-ethoxy-1,2-dihydro-2,2,4-trimethylquinoline.

15. A compound according to claim 1 being 1-(6-D-glucopyranosyloxycarbonyl)-6-ethoxy-1,2-dihydro-2,2,4-trimethylquinoline.

16. A compound according to claim 1 being 1-carbomethoxy-6-ethoxy-1,2-dihydro-2,2,4-trimethylquinoline.

17. A compound according to claim 1 being 1-(1-D-glucopyranosyloxycarbonyl)-6-ethoxy-1,2-dihydro-2,2,4-trimethylquinoline.

18. A compound according to claim 1 being 1-carboxamido-6-ethoxy-1,2-dihydro-2,2,4-trimethylquinoline.

19. A compound according to claim 1 being 1-carbobenzoxyglycoyl-6-ethoxy-1,2-dihydro-2,2,4-trimethylquinoline.

20. A compound according to claim 1 being 1-(carbobenzoxy-β-alanyl)-6-ethoxy-1,2-dihydro-2,2,4-trimethylquinoline.

21. A compound according to claim 1 being 1-glycyl-6-ethoxy-1,2-dihydro-2,2,4-trimethylquinoline.

22. A compound according to claim 1 being 1-glycyl-6-ethoxy-1,2-dihydro-2,2,4-trimethylquinoline tartrate.

23. A compound according to claim 1 being 1-(β-alanyl)-6-ethoxy-1,2-dihydro-2,2,4-trimethylquinoline.

24. A compound according to claim 1 being 1-(β-alanyl)-6-ethoxy-1,2-dihydro-2,2,4-trimethylquinoline tartrate.

25. A compound according to claim 1 being 1-(methyl tri-O-acetyl-D-glucopyranosylurono)-6-ethoxy-1,2-dihydro-2,2,4-trimethylquinoline.

26. A compound according to claim 1 being 1-(methyl-D-glucopyranosylurono)-6-ethoxy-1,2-dihydro-2,2,4-trimethylquinoline.

27. A compound according to claim 1 being 1-(D-glucopyranosyluronamido)-6-ethoxy-1,2-dihydro-2,2,4-trimethylquinoline.

28. A compound according to claim 1 being Di-(6-ethoxy-1,2-dihydro-2,2,4-trimethyl-1-quinolyl)-amido-2,3,4,5-tetra-O-acetyl-glactaric acid.

29. A pharmaceutical composition according to claim 1 comprising also an iron preparation.

30. A pharmaceutical composition according to claim 29, wherein the iron preparation is iron dextran.

31. Animal feed composition for use in treatment of Vitamin E-deficient animals, comprising an animal foodstuff and a compound of claim 1.

32. Liquid composition for use in treatment of Vitamin E-deficient animals, comprising drinking water and a compound of claim 1.

* * * * *